United States Patent [19]

O'Connor et al.

[11] Patent Number: 4,458,690
[45] Date of Patent: Jul. 10, 1984

[54] BLOOD PRESSURE MONITOR

[75] Inventors: Arthur H. O'Connor, Lancaster; Robert A. Rossman, Leola, both of Pa.

[73] Assignee: Novatec, Inc., Lancaster, Pa.

[21] Appl. No.: 381,429

[22] Filed: May 24, 1982

[51] Int. Cl.³ ............................................. A61B 5/02
[52] U.S. Cl. ..................................... 128/681; 128/680
[58] Field of Search ............... 128/672, 675, 677–678, 128/680–682, 685, 687, 689

[56] References Cited

U.S. PATENT DOCUMENTS

| | | | |
|---|---|---|---|
| 2,826,191 | 3/1958 | Burns | 128/682 |
| 2,865,365 | 12/1958 | Newland et al. | 128/681 |
| 2,875,750 | 3/1959 | Boucke et al. | 128/682 |
| 3,086,513 | 4/1963 | Newland et al. | 128/682 |
| 3,090,377 | 5/1963 | Salisbury et al. | 128/677 |
| 3,126,886 | 3/1964 | Karsh | 128/682 |
| 3,149,628 | 9/1964 | Bolie | 128/680 |
| 3,189,024 | 6/1965 | Smith | 128/682 |
| 3,224,435 | 12/1965 | Traite | 128/682 |
| 3,542,011 | 11/1970 | Langenbeck | 128/677 |
| 3,552,383 | 1/1971 | Krueger et al. | 128/682 |
| 3,585,987 | 6/1971 | Svensson | 128/672 |
| 3,633,568 | 1/1972 | Hobel | 128/682 |
| 3,654,915 | 4/1972 | Sanctuary | 128/682 |
| 3,779,235 | 12/1973 | Murphy, Jr. et al. | 128/682 |
| 3,885,551 | 5/1975 | Massie | 128/682 |
| 4,058,117 | 11/1977 | Kaspari et al. | 128/682 |
| 4,078,551 | 3/1978 | Wohltjen et al. | 128/681 |
| 4,105,020 | 8/1978 | Matsuoka et al. | 128/682 |
| 4,116,230 | 9/1978 | Gorelick | 128/682 |
| 4,117,835 | 10/1978 | Williams | 128/677 |
| 4,137,907 | 2/1979 | Jansen et al. | 128/681 |
| 4,167,181 | 9/1979 | Lee | 128/682 |
| 4,178,918 | 12/1979 | Cornwell | 128/682 |
| 4,245,648 | 1/1981 | Trimmer et al. | 128/672 X |
| 4,261,368 | 4/1981 | Danna et al. | 128/680 |
| 4,262,674 | 4/1981 | Uemura et al. | 128/680 |
| 4,347,851 | 9/1982 | Jundanian | 128/672 X |
| 4,378,807 | 4/1983 | Peterson et al. | 128/680 X |

FOREIGN PATENT DOCUMENTS 8103606 12/1981 European Pat. Off. ............ 128/672

Primary Examiner—Lee S. Cohen
Assistant Examiner—Angela D. Sykes
Attorney, Agent, or Firm—Martin Fruitman

[57] ABSTRACT

A digital readout electronic blood pressure and pulse rate monitor. A finger cuff occluder is pressurized by a single stroke plunger and an automatic vent means provides linear pressure decay while a pressure transducer measures the pressure and converts it to an electronic signal. A sound transducer senses sound transmitted from the cuff through the pressure tube, and an electronic system distinguishes the various characteristics of the sound to measure the systolic and diastolic pressures. The electronic system also measures the pulse rate. All three readings are digitally displayed only if several predetermined conditions indicating a proper reading are fulfilled.

22 Claims, 2 Drawing Figures

BLOOD PRESSURE MONITOR

SUMMARY OF THE INVENTION

This invention deals generally in medical diagnostic testing and more specifically with a blood pressure and pulse rate measuring device which includes an inflatable occluder to automatically raise the pressure of inflation above the user's systolic pressure.

In recent years the public interest in blood pressure and particularly the problems of and those caused by high blood pressure has increased significantly. It is not at all uncommon to see T.V. or hear radio advertisements warning people to have their blood pressure checked regularly and to warn them of the fact that high blood pressure gives no outward symptoms of its presence.

The awareness has even initiated such programs as dentists measuring their patient's blood pressure at every visit, and, more obviously, has resulted in coin operated blood pressure reading machines appearing in shopping center malls and stores. Moreover, many mail order catalogue outlets are now offering sphygmomanometer and stethoscope kits to permit self-monitoring of blood pressure.

While it is clear that no reading taken by non-medical personnel should be relied upon for judgments in regard to health, there can be some benefit derived from self-readings. The most important of these is that, together, the patient and the doctor will be better able to establish what reading is normal for a patient, and also what deviations are significant.

All common blood pressure measurements are made using the same technique. First the arterial blood flow to a part of the body, usually an arm, is blocked by an air pressurized cuff to which is attached a pressure measuring instrument. Then the pressure in the cuff is slowly reduced while listening for the pulse beat in the part of the body to which the flow has been stopped. The pressure noted in the cuff when a pulse beat is first heard is the systolic pressure and indicates that the heart generated blood pressure has just overcome the blockage caused by the external pressure. As the cuff pressure is further reduced, the blood pressure finally surpasses the external pressure at all times. At that time the pulse heard at the monitored point becomes indistinct due to relatively constant blood flow and the diastolic pressure is read from the external pressure meter.

The traditional arm cuff method of measurement, however, has many potential difficulties which usually cause considerable errors in its use as a self measuring instrument. Variations caused by cuff placement, an individual's arterial condition and body temperature, the ability to hear and distinguish sounds through a stethoscope, cuff pressurization and pressure leak rate all can cause errors in and between measurements.

The coin machines, although automatic, have an added fault in that they typically pressurize to a high level to accommodate the worst case, but therefore are extremely uncomfortable, even painful, for some users. Moreover, the considerable size and complexity of such automatic machines make them most unlikely as a home use appliance.

The present invention overcomes the difficulty of self testing blood pressure by the use of a sensitive electronic detector to pick up the sound of blood in the arteries and to distinguish the difference in the characteristics of that sound as the blood flow is stopped and begins again. Moreover, to facilitate self measurement, a finger cuff rather than an arm cuff, is used to make attachment and use more consistent and eliminate the need for special dexterity.

The present invention is specifically designed to permit inexperienced laymen to secure consistent reading on a small, portable, automatic device. In order to further this goal, the air pressure system includes a single stroke pump which inflates the finger cuff and a linear pressure decay mechanism which vents system pressure at a predictable and highly linear rate. Also, to preclude false readings, the electronic system of the Blood Pressure Monitor includes several circuits, each of which is specifically designed to aid in discrimination between noise signal and true blood pulse signals.

The first protection against noise is the use of a combination of the air pressure system and an electronic system to delay measurement until the system "settles down" after application of cuff pressure. This circuit does not use a time delay, but rather blocks any measurement until the cuff pressure, initially pressurized to 265 mm of mercury, decays to 210 mm. The measurement initiation is therefore not keyed to an artificial parameter such as time, but is controlled by pressure, one of the parameters actually measured.

The second noise eliminating circuit uses both high frequency and pulse channels in the measuring process and takes readings only when the combination of those two channels indicates that a legitimate reading is being sensed. The pulse information is attained by using the blood pressure impulse as it impinges on the side of the finger cuff nearest the hand, the side nearest the heart. This signal is not significantly affected by the blockage or release of blood flow in the finger, and is detectable both before the systolic pressure point and after the diastolic pressure point. The processing of this signal includes a threshold level detector, but the signal, once processed into a rectangular pulse shape, is present before and after readings are taken and is timed essentially simultaneously with the other information being sought. This signal is therefore used as a gate, and any signal which occurs in the system, but does not occur during the time determined by this gate, is blocked out.

The sensing of the systolic and diastolic points is dependent on a distinction in the frequency of the sound in the arteries. As the blood begins to flow past the occluder, the pressure cuff, high frequency sound is generated, similar to the sound heard when water flows past a faucet into a garden hose. This high frequency component is detected by means of a high pass filter in the electronic system, and is also subjected to a threshold level detector to eliminate the effects of some low level signals present before the systolic and diastolic pressure points.

The previously described pulse channel and the high frequency channel are then combined in an AND gate, and a true blood pressure pulse signal is only acknowledged and the systolic blood pressure reading recorded when both channels have measured a simultaneous pulse. This reading is not, however, displayed. Another error suppression system must first be satisfied.

A counting system is included in the electronics of the invention which negates any reading of systolic pressure which is not followed by four more legitimate pulses with time intervals of less than two seconds between all pulses. A simple isolated pulse reading will therefore not yield a false systolic pressure display.

Instead, the system will be reset and, providing proper conditions are met, await a legitimate signal.

An additional circuit is included in the invention to aid in detecting the diastolic pressure point. Since the audible signal level frequently decreases between the systolic and diastolic points, the threshold level for detection of diastolic pressure point is reduced from the level used to detect the systolic pressure point so that the lower signal strength of the change at the diastolic pressure point will not be lost. The dual threshold level yields more successful noise suppression at the systolic pressure point measurement and more sensitive operation at the lower signal intensity of the diastolic pressure point.

A particularly beneficial feature of the present invention is its means for detecting the audible signal from the arteries. To increase reliability by eliminating microphones in the pressure cuff with their attendant electrical cables connecting them to the display unit, the air pressure tube itself is used to transmit sound to a sensor mounted and protected well within the display unit. This also eliminates another noise sound, the connecting cables and their connections, since flexing and pulling on such arrangements is a common source of random electronic noise. Moreover, it permits the use of a large diaphragm on the pressure sensitive sensor and, therefore, yields a greater sensitivity than would otherwise be possible. The sensor's remoteness from the cuff also eliminates some of the effects of random audio noise associated with flexing of the external portions of the cuff. Essentially, sound produced at the pressure cuff is carried, along with pulse variations in air pressure due to compression of the cuff by blood pressure effects, to the interior of the display unit where a relatively large diameter piezoelectric diaphragm picks up the pressure variations and sound, and converts them into electrical signals.

As described above, these signals are specifically processed with particular emphasis on discrimination against erroneous signal. The results are displayed in digital form as three readings, systolic pressure, diastolic pressure and pulse rate. The results achieved by this system closely parallel those attained by personnel highly experienced in taking such measurements, but only because of the multiple discriminating circuits which, in effect, make the same decisions as would the experienced personnel, and make them consistently and accurately.

DETAILED DESCRIPTION OF THE INVENTION

Figure 1:
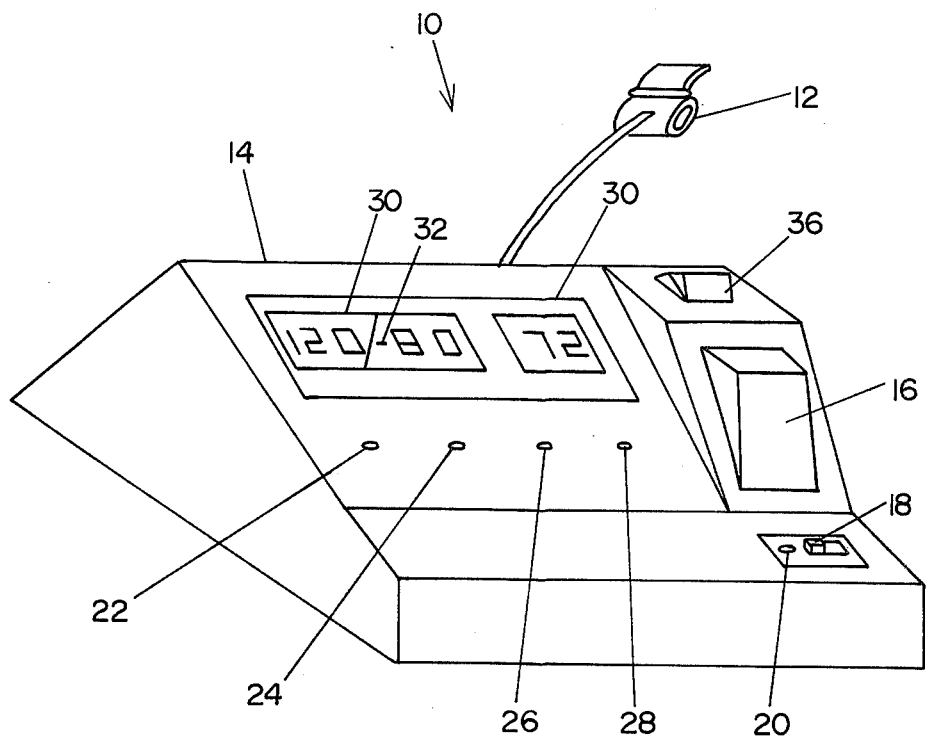
FIG. 1 is a perspective view of the preferred mechanical embodiment of the invention.

FIG. 1 depicts a perspective view of the preferred mechanical embodiment of the Blood Pressure Monitor 10 in which finger cuff 12, attached to display unit 14, is pressurized by one-stroke inflator 16. Blood pressure Monitor 10 is powered by rechargeable batteries mounted internally, whose drain is cut-off by power switch 18 when the unit is not in use. Light 20 indicates when power is on the unit. Four other lights 22, 24, 26 and 28 indicate various functions in the electronic circuit. Light 22 is lit when the air system is pressurized. Light 24 is activated while the electronic system is in the process of measuring blood pressure. Light 26 lights when the electronics is ready to measure or resets itself after an improper measurement sequence, and light 28 lights momentarily in synchronism with each blood pressure beat.

Numerical display 30 displays both the systolic and diastolic blood pressures and displays minus sign 32 as an indicator of low battery voltage. Numerical display 30 displays the measured heart pulse rate on its last three digits. Button 36 is a release button to depressurize the air system and release the user from finger cuff 12.

As will be described below, Blood Pressure Monitor 10 functions to comfortably and automatically read the systolic and diastolic blood pressure and the blood pulse rate while automatically verifying that it is indeed taking valid readings.

Figure 2:
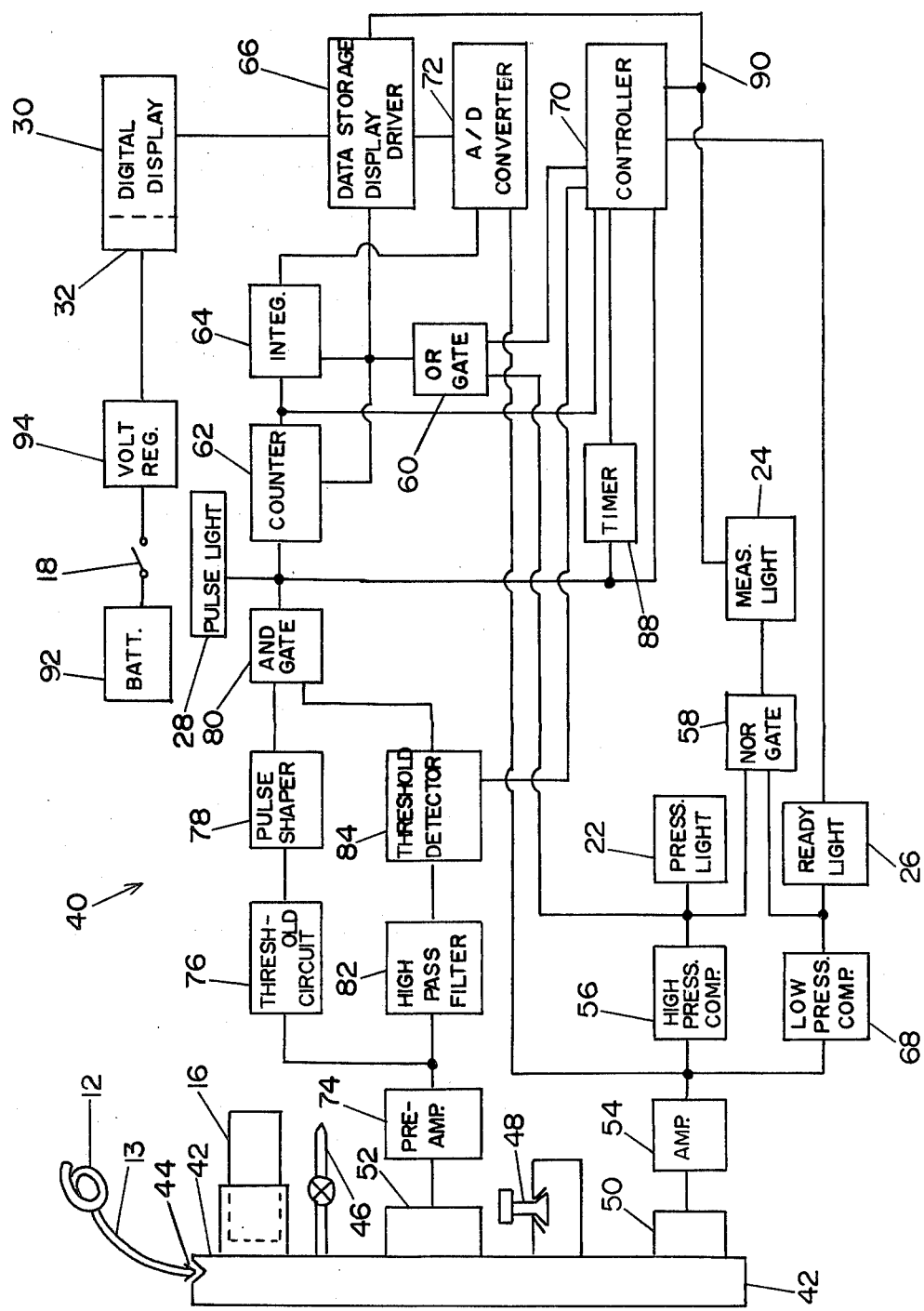
FIG. 2 is a simplified block diagram of the electronic circuit of the preferred embodiment of the invention.

FIG. 2 is a simplified block diagram of the electronic circuit of the preferred embodiment of the invention in which finger cuff 12 is used in conjunction with electronic circuit 40 to display the blood pressure information on digital display 30.

Finger cuff 12 is connected to air pressure manifold 42 at connector 44 where it may be disconnected for ease of storage or for interchange with a finger cuff of different size. Air pressure manifold 42 is pressurized by plunger 16, operated by the user after finger cuff 12 is properly positioned, to a pressure of approximately 265 mm. of mercury. Linear pressure decay mechanism 46 begins to bleed off the pressure in manifold 42 at the rate of approximately 3.5 mm. of mercury per second as soon as it is pressurized. Emergency pressure release 48 is available if the user should desire to deflate finger cuff 42.

The electronic circuitry interfaces with the pneumatic system by means of pressure transducer 50 and pulse transducer 52. Pressure transducer 50, typically consisting of a semiconductor strain guage, provides a voltage output proportioned to the air pressure of manifold 42. It therefore indicates the "steady state" air pressure.

Pulse transducer 52 on the other hand is constructed specially to sense short term perturbations in air pressure or "pulses". In effect, it acts much like a microphone and like the ear of the physician at one end of a stethoscope. It should be noted however that the air system being monitored for sound is not, as in a normal blood pressure measurement, an independent system with a column of still air, but rather the very same air system used to close off blood circulation.

The present invention senses and interprets, not what the physician would hear as he monitors the arteries beyond the point of blood restriction, but rather the sound that occur precisely at that restriction point, within finger cuff 12. This monitoring is, however, accomplished, not by using an additional sensing unit built into cuff 12. Rather, by using tubing 13 which connects the cuff to the monitoring unit, to both pressurize cuff 12 and to transmit air pressure pulses, which are caused by the sounds at the cuff, back to electronic circuit 40, a highly reliable sensing system is the result.

The dependability of the present invention is further enhanced by the particular electronic circuitry used, as is described below and pictured in FIG. 2.

One function of the circuit is to block out the likely noise and other false signals likely to occur during initial pressurization. This is accomplished by using the actual air pressure parameters as a "lock out" as compared to a more traditional time delay.

The pressure proportional voltage from pressure transducer 50 is amplified by amplifier 54 and fed to comparator 56. Comparator 56 is set to produce an output signal for a voltage input greater than the equivalent of 210 mm of mercury and no output signal if its input voltage is less.

Since operation of pressurization plunger 16 produces a manifold pressure of approximately 265 mm, upon initial pressurization comparator 56 will produce an output, and (1) activate pressure light 22; (2) produce an input at NOR gate 58 preventing measuring light 24 from operating; and (3) produce an input at OR gate 60. The output thus produced by OR gate 60 resets and inhibits the operation of counter 62, integrator 64 and data storage and display driver 66. This produces settling time and prevents the system from responding to any pressure transients that are generated by the shock of initial pressurization.

Meanwhile linear pressure decay mechanism 46 begins bleeding off air pressure at the rate of 3.5 mm of mercury per second, so that when, after about 15 seconds, the pressure falls from 265 mm. to 210 mm., the output of comparator 56 ceases and (1) pressure light 22 goes off; (2) the input to NOR gate 58 is removed, activating "measurement" light 24; and (3) the reset/inhibit signal is removed from counter 62, integrator 64 and data storage and display driver 66.

Measuring light 24 will remain on as long as the pressure, sensed by low pressure comparator 68, remains above approximately 50 mm., unless a special signal is received from controller 70, because low pressure comparator 68 generates an input to NOR gate 58. If the pressure falls below 50 mm., low pressure comparator 68 also activates ready light 26 to indicate to the operator that the system should be pressurized again.

Throughout the entire pressurization cycle the output of amplifier 54 is also fed to analog to digital converter 72, where it is converted to digital format and forwarded to data storage and display driver 66. The pressure reading at any point in the sequence can then be forwarded to digital display 30 and displayed as either systolic or diastolic pressure as required by controller 70.

When the inhibit signal from OR gate 60 is terminated, the actual measuring sequence begins, based on the pulse information picked up by pulse transducer 52 and amplified by preamplifier 74. These signals are then analyzed according to the expected characteristics of the audible information available from the arteries.

One component of the sound from the arteries is the pulse beat detectable as the heart pumped blood pulse impinges on the finger cuff on the heart side of the cuff. This component is present at all times, both before the systolic point and after the diastolic point. It is used as a primary control by circuit 40. Pulse threshold circuit 76 detects it and feeds pulse shaper 78 which produces a standard amplitude pulse of 100 millisecond duration for use as a gate pulse.

This pulse is fed to AND gate 80 which will only produce an output if it receives a signal on its other input simultaneously with the gate pulse. Therefore, no subsequent signal processing occurs unless both the gate pulse caused by the blood impinging on the finger cuff and the signal on the other AND gate 80 input are present at the same time.

The second signal is also derived from pulse transducer 52 via preamplifier 74, but is analyzed for different characteristics. High pass filter 82 is used to verify that the pulse transducer is detecting signal frequencies higher than 45 Hz, indicating that the systolic pressure point is just being matched, and some blood is flowing past finger cuff 12 at the maximum of each pulse of blood pressure. The higher frequencies then generated in the finger by this blood flow are transmitted to finger cuff 12 and are picked up by pulse transducer 52, amplified by preamplifier 74, and presented to the input of high pass filter 82. High pass filter 82 is followed by threshold detector 84 which verifies that a minimum level of input signal has been achieved before it generates an output signal to AND gate 80.

When AND gate 80 receives input from both pulse shaper 78 and threshold detector 84 at the same time, meaning that both a heart beat pulse and the sound of blood flow have been detected, AND gate 80 produces an output pulse. Each time this pulse occurs, pulse light 28 lights momentarily, but the AND gate 80 output also is fed to counter 62, timer 88 and controller 70.

The first such input into controller 70 causes it to command analog to digital converter 72 to forward the pressure reading then available to data storage and display driver 66. This pressure information, which is the systolic pressure, is placed in the memory of data storage and display driver 66, but not yet displayed, since several other criteria must first be met.

At this first pulse, controller 70 also changes the level of sensitivity of threshold detector 84 to 80% of its previous levels. This permits the detection of the later diastolic pressure point, which occurs at a lower signal level than the previous systolic pressure point, while the higher initial threshold level of sensitivity better assured discriminating against false indications of the systolic point which has a stronger signal level.

The first pulse from AND gate 80 also sets the output of timer 88 to its high level. Timer 88 will remain at this high output level for two seconds and then its output will drop back to its original low level. If this occurs the negative pulse to controller 70 causes it to transmit a signal to OR gate 60 which momentarily resets counter 62, integrator 64 and data storage and display driver 66, thus preventing the display of systolic pressure due to the single pulse.

If, however, a second pulse occurs within two seconds this reset sequence is delayed for another two seconds, and a sequence of pulses with a pulse period of less than two seconds postpones this reset system indefinitely. Counter 62 thus acts as an additional noise discrimination system, since it requires a sequence of proper pulses within a predictable time before a systolic pressure reading can be displayed.

The output pulse from AND gate 80 is also fed to counter 62 to further verify and ultimately display the pressure reading at the systolic pressure point. The output of counter 62 goes to a high level and is set to remain at that level until it receives four more input pulses at which time it returns to its original zero level. Counter 62 output is fed to integrator 64 whose output is therefore a continuously increasing ramp voltage which increases until the output of counter 62 ceases.

At that time the decreasing output of counter 62 is also transmitted to controller 70 which commands analog to digital converter 72, to which the output of integrator 64 is sent, to read the output of integrator 64 into the memory of data storage and display driver 66. The output of integrator 64, being proportional to the time it took to accumulate four heartbeat pulse periods, is an inverse measure of the pulse rate. When it is applied to the "reference" input of analog to digital converter 72 the resulting data obtained is the inverse of the period, the actual pulse rate.

If, because of noise signals or some other reason the five pulses required by integrator 64 are not accumulated or there is a period of greater than two seconds between any two pulses, timer 88 will abort the reading, as described above, and no read command will be given by controller 70.

To this point no numerals have appeared upon digital display 30 and the user has only seen pressure light 22 go on and then go off as measuring light 24 went on, and pulse light 28 has been lighting momentarily with each heart pulse beat.

As the pressure in the system continues to decrease, output pulses continue to appear at the output of AND gate 80 until the diastolic pressure point is reached. At this point a change occurs in the signals received by pulse transducer 52. When finer cuff 12 no longer acts as a restriction on blood flow, that is, when even the lowest blood pressure surpasses the air pressure in finger cuff 12, the higher frequency signals stop. More accurately, they reduce dramatically and fall below the new threshold level for which threshold detector 84 has been set. Therefore, threshold detector 84 no longer furnishes an output to AND gate 80 and no output from AND gate 80 is furnished to pulse light 28, counter 62, timer 88 and controller 70.

Since timer 88 receives no subsequent pulses its output drops after two seconds, and since counter 62 has already fulfilled its full count and furnished controller 70 with the command to read the blood pulse rate, controller 70 commands analog to digital converter 72 to furnish the pressure reading to data storage and display driver 66. This reading is the diastolic pressure. When controller 70 has commanded data storage and display driver 66 to accummulate each of the three required readings, systolic pressure, pulse rate and diastolic pressure, it follows the last command with a read command to data storage and display driver 66 to display all three readings on digital display 30 by providing a signal on line 90. This signal also turns off measuring light 24 and the measuring sequence is then complete.

A final precaution built in the system is that if controller 70 receives no read command before the air pressure in the system falls below 50 mm. of mercury, comparator 68 will give an output. This activates ready light 26 and is transmitted to controller 70 to prevent a read command, and also inputs to NOR gate 58 which deactivates measuring light 24. This essentially notifies the user that the system must be repressurized and another attempt made at securing the readings.

Battery 92 and voltage regulator 94 are connected through switch 18 and power all the electronic curcuits in the Blood Pressure Monitor. Low voltage indicator 32 is connected to the voltage regulator and is built into digital display 30 where it lights in the form of a minus sign if the battery voltage falls below the level required for dependable operation.

The combination of the several self-checking circuits and the easily used finger cuff yields a particularly useful instrument for use by the unskilled layman, which when used along with professional consultation can be a valuable aid to a program of blood pressure study or control.

It is to be understood that the form of this invention as shown is merely a preferred embodiment. Various changes may be made in the function and arrangement of parts. Equivalent means may be substituted for those illustrated and described, and certain features may be used independently from others without departing from the spirit and the scope of the invention as defined in the following claims. For instance the specific number of pulses counted to verify proper functioning or the specific two second time delay might be changed under certain circumstances, and the power source used could be line voltage and a rectifier circuit instead of batteries.

What is claimed as new and desired to be secured by Letters Patent of the United States is:

1. A blood pressure measuring apparatus comprising:
   a manifold pressurizable with a compressed gas;
   pressurization means connected to the manifold to apply compressed gas to the manifold;
   linear pressure decay means connected to the manifold;
   blood flow occluder means connected to the manifold and configured to block arterial blood flow of the user;
   gas connection means, which is the only means interconnecting the occluder means and the manifold, and which transmits sound and gas pressure pulses from the occluder means to the manifold and interchanges gas flow and pressure between the manifold and the occluder means;
   pressure transducer means connected to the manifold and yielding an electrical signal varying in amplitude with the static pressure in the manifold;
   pulse transducer means connected to the manifold and yielding an electrical signal varying in amplitude and frequency with sound and gas pressure pulses in the manifold;
   electronic circuit means, connected to the pressure transducer means and the pulse transducer means, by non-flexible connections, measuring the systolic and diastolic pressure points by determining the pressure values, as measured by the pressure transducer means, at which the sound and gas pressure pulses derived from the pulse transducer means change characteristics; and
   display means connected to the electronic circuit means, and displaying the systolic and diastolic pressures measured by the electronic circuit means.

2. A blood pressure measuring apparatus as in claim 1 wherein the occluder means is a finger cuff.

3. A blood pressure measuring apparatus as in claim 1 wherein the pressurization means is a pump which pressurizes the manifold with a single stroke.

4. A blood pressure measuring apparatus as in claim 1 further comprising a manually operated valve connected to the manifold which releases all gas pressure from the manifold and occluder means when operated.

5. A blood pressure measuring apparatus as in claim 1 further comprising pulse rate measuring means within the electronic circuit means to determine the rate of blood pressure pulses from the pulse transducer means output and connected to additional display means which displays the pulse rate.

6. A blood pressure measuring apparatus of claim 5 wherein the pulse rate measuring means comprises an integrator receiving signals from the pulse transducer means for a predetermined number of pulses and a mathematical inversion circuit connected to and receiving the integrator output, inverting the integrator signal and transmitting it to the additional display means.

7. The blood pressure measuring apparatus of claim 1 wherein the electronic circuit means includes pressure operated delay means comprising lock-out means to prevent operation of the electronic circuit means, other than the lock-out means, when the manifold is pressurized above a predetermined level; high pressurization means wherein the pressurization means includes high pressure means to assure that normal initial pressurization surpasses the predetermined level; and decay delay means wherein the linear pressure decay means operates to delay the reduction of pressure to below the predetermined level until after initial pressure transients in the manifold have essentially dissipated.

8. The blood pressure measuring apparatus of claim 7 wherein the pressure operated delay means comprises a higher pressure comparator receiving signals from the pressure transducer means and a gate circuit connected to the higher pressure comparator, the gate circuit preventing other portions of the elctronic circuit means from functioning.

9. The blood pressure measuring apparatus of claim 1 wherein the electronic circuit means includes gating means comprising means to verify that the pulse transducer means is sensing both pulse and high frequency components before the output signal of the pulse transducer means is processed to display readings.

10. The blood pressure measuring apparatus of claim 9 wherein the gating means comprises a pulse threshold circuit and a high pass filter circuit, both receiving signals from the pulse transducer means; a pulse shaping circuit connected to the pulse threshold circuit; a threshold detector circuit connected to the high pass filter circuit; and an AND gate circuit with inputs connected to both the threshold detector circuit and the pulse shaping circuit and its output connected to and feeding electronic systems to measure and display the readings.

11. The blood pressure measuring apparatus of claim 1 wherein the electronic circuit means includes counting means to verify that the pulse transducer means senses a predetermined number of blood pressure pulses before the output signal of the pulse transducer means is processed to display readings.

12. The bood pressure measuring apparatus of claim 11 wherein the counting means comprises a counter means receiving an input signal originated by the pulse transducer means, connected to and supplying a predetermined number of pulses to an integrator means, and wherein the output of the integrator means is connected to and furnishes an input signal to an inverter means to convert the integrator means output to a pulse rate reading.

13. The blood pressure measuring apparatus of claim 1 wherein the electronic circuit means includes timing means to verify that the output signal of the pulse transducer means contains pulses with no greater than a predetermined period between them before the signal is processed to display readings.

14. The blood pressure measuring apparatus of claim 13 wherein the timing means comprises a timer which times out in a predetermined time and upon timing out resets the electronic circuit means to reinitiate signal processing.

15. The blood pressure measuring apparatus of claim 1 wherein the electronic circuit means includes low pressure lock-out means to prevent electronic processing of signals from the pulse transducer means and the pressure transducer means if the manifold pressure falls below a predetermined level.

16. The blood pressure measuring apparatus of claim 15 wherein the low pressure lock-out means comprises a low pressure comparator receiving signals from the pressure transducer means and a gate circuit connected to the low pressure comparator, the gate circuit preventing electronic processing of signals from the pulse transducer means.

17. The blood pressure measuring apparatus of claim 1 wherein the electronic circuit means means includes threshold modification means to increase the sensitivity of the electronic circuit to changes in the output signal of the pulse transducer means after the systolic pressure point is measured and before the diastolic pressure point is anticipated.

18. The blood pressure measuring apparatus of claim 11 wherein the threshold modification means comprises means to increase the sensitivity of the electronic circuit means by lowering the threshold level at which the electronic circuit means ceases to respond to the signal from the pulse transducer means to no more than 80 percent of the threshold level at which the electronic circuit means began to respond to the signal from the pulse transducer means.

19. The blood pressure measuring apparatus of claim 1 wherein the display means is a digital display and includes an indicator identifying low voltage from a power source which powers the electronic circuit means.

20. The blood pressure measuring apparatus of claim 1 further comprising an indicator light connected to the electronic circuit means which activates when the manifold is pressurized above a predetermined level.

21. The blood pressure measuring apparatus of claim 1 further comprising an indicator light connected to the electronic circuit means which activates when the electronic circuit means is in the process of making a measurement.

22. The blood pressure measuring apparatus of claim 1 further comprising an indicator light connected to the electronic circuit means which activates momentarily as each blood pressure pulse is sensed by the pulse transducer means.

* * * * *